US011103314B2

(12) United States Patent
Abhari et al.

(10) Patent No.: US 11,103,314 B2
(45) Date of Patent: Aug. 31, 2021

(54) METHODS AND DEVICES FOR TRACKING OBJECTS BY SURGICAL NAVIGATION SYSTEMS

(71) Applicant: Synaptive Medical Inc., Toronto (CA)

(72) Inventors: Kamyar Abhari, Toronto (CA); Kai Michael Hynna, Toronto (CA); Gal Sela, Toronto (CA); Kirusha Srimohanarajah, Toronto (CA)

(73) Assignee: Synaptive Medical Inc., Toronto (CA)

( * ) Notice: Subject to any disclaimer, the term of this patent is extended or adjusted under 35 U.S.C. 154(b) by 951 days.

(21) Appl. No.: 15/821,985

(22) Filed: Nov. 24, 2017

(65) Prior Publication Data

US 2019/0159841 A1 May 30, 2019

(51) Int. Cl.
*A61B 34/20* (2016.01)
*G16H 20/40* (2018.01)
(Continued)

(52) U.S. Cl.
CPC .............. *A61B 34/20* (2016.02); *G16H 20/40* (2018.01); *G16H 30/40* (2018.01); *A61B 34/30* (2016.02);
(Continued)

(58) Field of Classification Search
CPC .......... G16H 30/40; G16H 30/20; G06T 7/70; A61B 34/20; A61B 34/30; A61B 2034/2051; A61B 2034/2048; A61B 2034/2072; A61B 2034/2055; A61B 2034/2057; A61B 2034/2065;
(Continued)

(56) References Cited

U.S. PATENT DOCUMENTS 9,541,383 B2   1/2017   Abovitz et al.
9,671,566 B2   6/2017   Abovitz et al.
(Continued)

FOREIGN PATENT DOCUMENTS

WO   2016207628 A1   12/2016

OTHER PUBLICATIONS

Search Report issued by the Intellectual Property Office of the United Kingdom in relation to corresponding GB Application GB1818984.5 dated May 21, 2019, 4 pgs.

*Primary Examiner* — Christopher Koharski
*Assistant Examiner* — Katherine M McDonald
(74) *Attorney, Agent, or Firm* — Rowand LLP

(57) ABSTRACT

A method and device for tracking objects by surgical navigation systems. The method includes: capturing an image of the tracked object; determining whether a unique identifiable feature associated with at least one totem pattern is discernible in the image; when the unique identifiable feature is discernible: determining a position or an orientation of the tracked object based on the at least one totem pattern; and registering the at least one totem pattern in the surgical coordinate space; and when the unique identifiable feature is indiscernible: determining a position of each totem pattern relative to other totem patterns such that a combination of totem patterns within the captured image is a marker group detectable as a composite totem pattern; determining a position or an orientation of the tracked object based on the composite totem pattern associated with the tracked object; and registering the composite totem pattern in the surgical coordinate space.

10 Claims, 11 Drawing Sheets

(51) Int. Cl.
*G16H 30/40* (2018.01)
*G16H 30/20* (2018.01)
*A61B 90/00* (2016.01)
*A61B 90/50* (2016.01)
*A61B 34/30* (2016.01)
*A61B 17/00* (2006.01)

(52) U.S. Cl.
CPC ............. *A61B 90/361* (2016.02); *A61B 90/37* (2016.02); *A61B 2017/00207* (2013.01); *A61B 2034/2048* (2016.02); *A61B 2034/2051* (2016.02); *A61B 2034/2055* (2016.02); *A61B 2034/2057* (2016.02); *A61B 2034/2065* (2016.02); *A61B 2034/2072* (2016.02); *A61B 2090/363* (2016.02); *A61B 2090/365* (2016.02); *A61B 2090/372* (2016.02); *A61B 2090/502* (2016.02); *G16H 30/20* (2018.01)

(58) Field of Classification Search
CPC ........ A61B 2090/365; A61B 2090/363; A61B 2090/372; A61B 2090/502; A61B 90/37; A61B 90/361; A61B 2017/00207
See application file for complete search history.

(56) References Cited

U.S. PATENT DOCUMENTS

| | | | |
|---|---|---|---|
| 10,108,833 B2* | 10/2018 | Hong | G01S 17/74 |
| 2004/0138556 A1* | 7/2004 | Cosman | A61B 90/10 |
| | | | 600/424 |
| 2009/0111888 A1 | 9/2009 | Aoude et al. | |
| 2010/0092079 A1 | 4/2010 | Aller et al. | |
| 2015/0071851 A1 | 5/2015 | Jajal et al. | |
| 2016/0078627 A1 | 3/2016 | Daon et al. | |
| 2016/0331460 A1 | 11/2016 | Cheatham, III et al. | |
| 2018/0092698 A1* | 4/2018 | Chopra | G06F 1/163 |
| 2018/0120553 A1* | 5/2018 | Leshem | G02B 21/34 |
| 2019/0038365 A1* | 2/2019 | Soper | A61B 90/39 |

\* cited by examiner

METHODS AND DEVICES FOR TRACKING OBJECTS BY SURGICAL NAVIGATION SYSTEMS

FIELD

The present application generally relates to surgical navigation systems and, in particular, to methods and devices for tracking objects.

BACKGROUND

Surgical navigation systems may include optical imaging devices for detecting objects within a surgical navigation space. The surgical navigation systems may rely on reference markers for identifying tracked objects and for determining position or orientation of the tracked object. When the position or the orientation of a tracked object is determined, surgical navigation systems may register captured images in a prescribed coordinate space such that the captured image data may be compared or integrated with other data for presentation on a common display device.

BRIEF SUMMARY

In one aspect, the present application describes a method of tracking an object in a surgical coordinate space by a surgical navigation system including an optical imaging device, the tracked object having a reference body affixed thereto, the reference body comprising a substrate and a first layer affixed to the substrate, the first layer including a plurality of totem patterns, each totem pattern having a unique identifiable feature distinguishing that totem pattern from another totem pattern in the plurality of totem patterns. The method includes capturing an image of the tracked object, the image including image data associated with at least one totem pattern; determining whether a unique identifiable feature associated with at least one totem pattern is discernible in the image; when the unique identifiable feature associated with at least one totem pattern is discernible: determining a position or an orientation of the tracked object in the surgical coordinate space based on the at least one totem pattern; and registering the at least one totem pattern associated with the tracked object in the surgical coordinate space; and when the unique identifiable feature associated with at least one totem pattern is indiscernible: determining a position of each totem pattern relative to other totem patterns in the captured image such that a combination of totem patterns within the captured image is a marker group detectable by the surgical navigation system as a composite totem pattern; determining a position or an orientation of the tracked object in the surgical coordinate space based on the composite totem pattern associated with the tracked object; and registering the composite totem pattern associated with the tracked object in the surgical coordinate space.

In another aspect, the present application describes a reference body affixable to objects tracked by a surgical navigation system. The reference body includes: a substrate having a substrate surface area; a first layer affixed to the substrate, the first layer including a first totem pattern at a first position centered at an origin of orientation axes, the first totem pattern including a unique identifiable feature distinguishing the first totem pattern from another totem pattern; and a retroreflective portion affixed to the substrate at a second position from the origin position, wherein the retroreflective portion is detectable by an optical imaging device of the surgical navigation system for determining position information of the reference body in a surgical navigation coordinate space.

In another aspect, the present application describes a reference body affixable to objects tracked by a surgical navigation system. The reference body includes: a substrate; a first layer affixed to the substrate, the first layer including a first totem pattern at a first position centered at an origin of orientation axes, the first totem pattern including a unique identifiable feature distinguishing the first totem pattern from another totem pattern; and at least one touchpoint divot for touch point registration of the first totem pattern, the at least one touchpoint divot being a through-hole in the first layer and being associated with the first totem pattern, the at least one touchpoint divot being positioned at a respective known distance from the origin.

In another aspect, the present application describes a surgical navigation system to track an object in a surgical coordinate space, the tracked object having a reference body affixed thereto, the reference body comprising a substrate and a first layer affixed to the substrate, the first layer including a plurality of totem patterns, each totem pattern having a unique identifiable feature distinguishing that totem pattern from another totem pattern in the plurality of totem patterns. The surgical navigation system includes: a processor; an optical imaging device coupled to the processor; and a memory coupled to the processor and storing processor-readable instructions that, when executed, cause the processor to: capture an image of the tracked object, the image including image data associated with at least one totem pattern; determine whether a unique identifiable feature associated with at least one totem pattern is discernible in the image; when the unique identifiable feature associated with at least one totem pattern is discernible: determine a position or an orientation of the tracked object in the surgical coordinate space based on the at least one totem pattern; and register the at least one totem pattern associated with the tracked object in the surgical coordinate space; and when the unique identifiable feature associated with at least one totem pattern is indiscernible: determine a position of each totem pattern relative to other totem patterns in the captured image such that a combination of totem patterns within the captured image is a marker group detectable by the surgical navigation system as a composite totem pattern; determine a position or an orientation of the tracked object in the surgical coordinate space based on the composite totem pattern associated with the tracked object; and register the composite totem pattern associated with the tracked object in the surgical coordinate space.

In another aspect, the present application describes processor-readable instructions that, when executed, configure a processor to perform one or more of the operations described herein. In this respect, the term processor is intended to include all types of processing circuits or chips capable of executing program instructions.

Other aspects and features of the present application will be understood by those of ordinary skill in the art from a review of the following description of examples in conjunction with the accompanying figures.

BRIEF DESCRIPTION OF THE DRAWINGS

Reference will now be made, by way of example, to the accompanying drawings which show example embodiments of the present application.

Similar reference numerals may have been used in different figures to denote similar components.

DESCRIPTION OF EXAMPLE EMBODIMENTS

Figure 1:
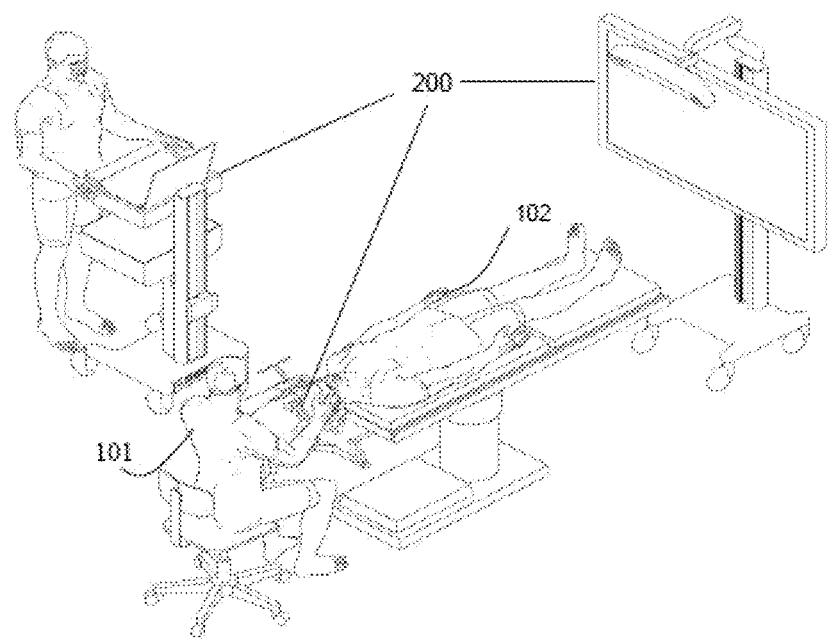
FIG. 1 illustrates a perspective view of a surgical navigation system, in accordance with an example of the present application.

Various examples and aspects of the present application will be described with reference to the details discussed below. The following description and drawings are illustrative of the present application and are not to be construed as limiting the present application. Numerous details are described to provide a thorough understanding of various embodiments. However, in certain instances, well-known or conventional details are not described in order to provide a concise discussion of the embodiments of the present application.

As used herein, the terms "comprises" and "comprising" are to be construed as being inclusive and open ended, and not exclusive. Specifically, when used in the specification and claims, the terms "comprises" and "comprising" and variations thereof mean the specified features, steps, or components are included. These terms are not to be interpreted to exclude the presence of other features, steps, or components.

As used herein, the term "exemplary" means "serving as an example, instance, or illustration", and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

The term "registration" or the expression "image registration" refers to the process of determining a transform to be used in correlating points across different coordinate systems. For example, the term registration may refer to determining a transform for correlating three-dimensional points across Cartesian coordinate systems. For example, registration may link points in a navigation coordinate space to an image coordinate space such that data positioned in one coordinate system may be mapped to another coordinate system using the transform. Data may include photographs, data from different sensors, times depths, or viewpoints. The process of registration is used in some examples for medical imaging in which images from different imaging modalities are co-registered. Registration may be utilized to compare or integrate data obtained from different modalities for presentation on a common platform or display.

It will be appreciated that there may be numerous registration techniques and one or more of the registration techniques may be applied to examples of the present application. Non-limiting examples include intensity-based methods that may compare intensity patterns in images via correlation metrics. Feature-based methods may identify correspondence between image features such as points, lines, and contours. Image registration methods may be classified according to transformation models used to relate a target image space to a reference image space. Classifications may be made between single-modality and multi-modality methods. Single-modality registration methods may register images in the same modality acquired by the same scanner or sensor type. For example, a series of magnetic resonance (MR) images may be co-registered. Multi-modality registration methods may be used to register images acquired by different scanner or sensor types. For example multi-modality registration methods may register an image obtained with magnetic resonance imaging (MRI) technology with an image obtained with positron emission tomography (PET) technology. Multi-modality registration methods may be used, for example, with medical imaging of the head and/or brain, the spine, or other portions of a patient, where images of the patient may commonly be obtained from different types of scanners or imaging devices. For example, registration may correlate computerized tomography (CT) and MRI images, or may correlate PET and CT images for tumor localization, or may correlate contrast-enhanced CT images with non-contrast-enhanced CT images, or may correlate ultrasound images with CT images.

In some examples, surgical navigation systems may identify tracked objects or determine position and/or orientation of a tracked object based on an individual reference marker. Detection of a reference marker may include visual detection by an optical imaging device. Reference markers can include identifiable symbols, patterns, text, an arrangement of marks within a unique pattern, or the like. For example, reference markers may be known as totems or totem patterns. Surgical navigation systems may also identify markers and determine position or orientation of tracked objects based on a combination of discrete reference markers spatially arranged in a pre-determined configuration.

However, surgical navigation systems depending on visual detection of reference markers may encounter challenges in numerous scenarios, including when: (1) reference markers are visually imperceptible within captured images (e.g., reference markers in captured images are out of focus or are too small to discern); or (2) a subset of reference markers in a combination of spatially arranged reference markers for determining position or orientation are not captured within captured images. It may be desirable to provide methods, devices, or systems to address challenges when visually detecting or tracking objects using a surgical navigation system.

In an aspect, the present application provides a method of tracking an object in a surgical coordinate space, where the tracked object may include a reference body affixed thereto. The reference body may include a substrate and a first layer affixed to the substrate. The first layer may include a plurality of totem patterns. Each totem pattern may have a unique identifiable feature distinguishing that totem pattern from another totem pattern in the plurality of totem patterns. A position of each totem pattern relative to other totem patters in the plurality of totem patterns may be pre-configured or pre-arranged. The method may include capturing an image of the tracked object and determining whether a unique identifiable feature associated with at least one totem pattern is discernible in the image. Further, when the unique identifiable feature of at least one totem pattern is discernible, the method may include determining a position or an orientation of the tracked object in the surgical coordinate space based on the at least one totem pattern. Further, when the unique identifiable feature of at least one totem pattern is indiscernible, the method may include determining a position of each totem pattern relative to other totem patterns in the captured image such that a combination of totem patterns is a marker group detectable as a composite totem pattern and determining a position or an orientation of the tracked object based on the composite totem pattern associated with the tracked object.

Reference is now made to FIG. 1, which illustrates a perspective view of a surgical navigation system 200. The surgical navigation system 200 may be positioned in an operating room (OR) for guiding a medical professional conducting a surgical procedure. In the example illustrated in FIG. 1, the medical professional 101 may conduct a minimally-invasive access port based surgical procedure on a patient 102 in the OR environment. The surgery may be in the field of neurosurgery and the medical professional 101 may be positioned adjacent a head of the patient 102. Although the OR environment illustrated in FIG. 1 is setup for conducting a neurosurgical procedure, in some other examples, the OR environment may be setup for other types of medical procedures, such as spinal surgery.

In addition to the surgical navigation system 200, the OR environment may include other equipment, such as surgical tool trays, carts, and booms. Some example equipment may include surgical lights, oxygen or other gas supplies, anesthesia supplies, etc.

Figure 2:
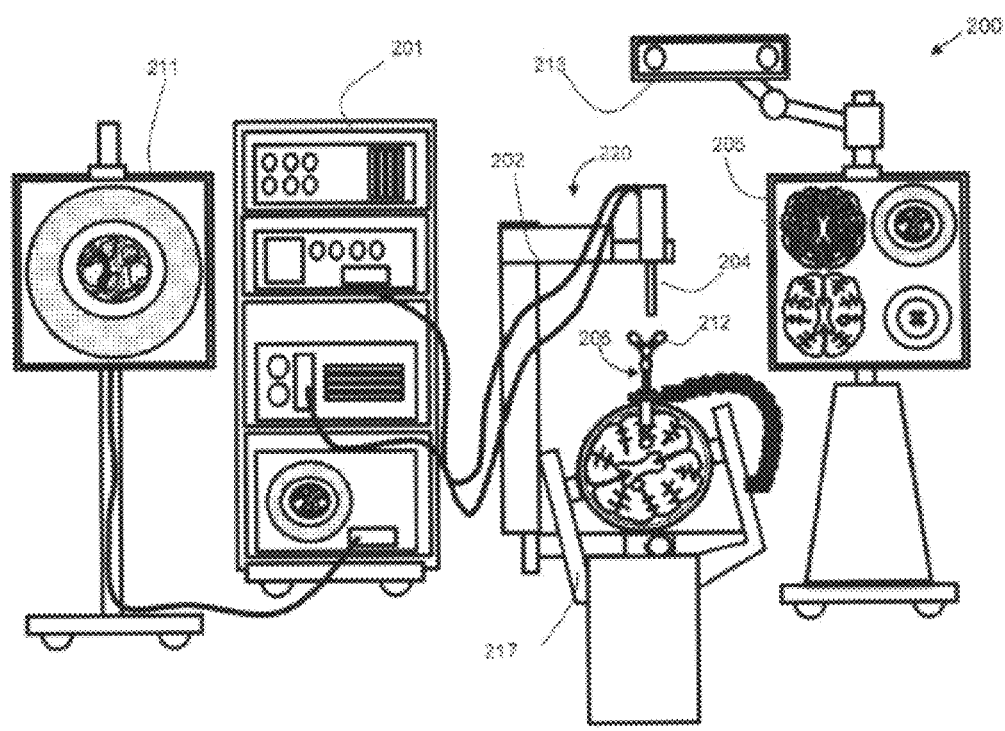
FIG. 2 illustrates further components of the surgical navigation system of FIG. 1, in accordance with an example of the present application.

Reference is now made to FIG. 2 which illustrates further components of the surgical navigation system 200 of FIG. 1, in accordance with an example of the present application. The surgical navigation system 200 may include an equipment tower 201, a tracking system 213, and at least one display device, such as a primary display device 211 and a secondary display device 205. The tracking system 213 may include optical imaging devices, such as cameras. In the example illustrated in FIG. 2, the tracking system 213 may include two laterally spaced-apart cameras for stereoscopic image capture. The cameras may be three-dimensional (3D) optical tracking stereo cameras, such as Northern Digital Imaging® (NDI) optical tracking stereo cameras. The surgical navigation system 200 may be configured to track at least one instrument, such as an access port 206, for assisting a medical professional 101 (FIG. 1) during a surgical procedure.

The surgical navigation system 200 may also include a device positioning unit 220. The device positioning unit 220 may include a robotic arm 202 that supports an optical device, such as an optical scope 204 or camera. The optical scope 204 may be positioned in line with a trajectory of access (co-axial with the access port 206) to enable the medical professional 101 (FIG. 1) to have visual sight through the access port 206. In examples where the optical scope 204 may include an image sensor, such as a camera, images from the optical scope 204 may be displayed on at least one of the primary display device 211 or the secondary display device 205. In some examples, the view or visual sight through the access port 206 may be integrated with other data, including pre-surgical plan information or pre-surgical imaging information (e.g., MRI, CAT scan, or ultrasound imaging information), and the added information may be registered based on registration of the patient 102 (FIG. 1) in the OR environment and/or registration of equipment relative to the patient 102. The surgical navigation system 200 may also track surgical instruments, such as the access port 206 or other tools in the OR environment. The surgical navigation system 200 may map models of the surgical instruments to a virtual space to which patient data may be mapped for rendering a combined display of the surgical instruments and the patient data and/or pre-surgical imaging data on at least one of the primary display device 211 or the secondary display device 205.

The equipment tower 201 may be mountable on a frame, such as a rack or a cart. The equipment tower 201 may be configured to accommodate, for example, a computer including a non-transitory, computer-readable storage medium comprising processor-executable instructions and a processor executing the processor-executable instructions. The processor-executable instructions may include, for example, surgical planning instructions, navigation instructions, robot control instructions, or any other types of instructions. The equipment tower may include other devices or components, such as power supplies, display panels, or printing devices.

In some examples, the surgical navigation system 200 may include a patient head mount 217 for retaining the patient in a position. For example, during a craniotomy procedure, a dura flap may be formed and retracted and the access port 206 may be inserted into the skull region of the patient. The tracking system 213 may track and determine location data of one or more equipment or objects in the OR environment. For example, the tracking system 213 may track, in real-time, a robotic arm 202 or surgical equipment, such as the access port 206. In some examples, tracked equipment may include at least one reference marker or fiducial marker 212 affixed thereto. For example, the fiducial marker 212 may be affixed to the access port 206 for tracking any movement, if any, of the access port 206 and for tracking objects moving within the vicinity of the access port 206.

The secondary display device 205 may be configured to display real-time information of the surgical navigation system 200. The displayed information may include multiple views of an instrument or of a portion of the patient. For example, the displayed information may include axial views, sagittal views, coronal views, or other types of views of instruments or portions of the patient.

In some examples, the fiducial marker 212 may include reflective spheres detectable by the tracking system 213, and the tracking system 213 may be an optical imaging device. For example, the tracking system 213 may detect electromagnetic emissions and the fiducial marker 212 may be an electromagnetic-based marker. The tracking system 213 may track a position of the fiducial marker 212 in a three-dimensional coordinate space, and the surgical navigation system 200 may be configured to correlate the position to a virtual coordinate space, thereby positioning a model of a tracked instrument in a virtual coordinate space.

Other types of fiducial markers, such as radio-frequency (RF), electromagnetic (EM), or light emitting diode (LED) (pulsed and un-pulsed) markers may be used. RF or EM markers may include specific signatures for uniquely identifying specific tools. In other examples, fiducial markers may include glass spheres, reflective stickers, or other unique structures and patterns. In some examples, reflective stickers, glass spheres, or LED markers may be detected using optical detectors, while RF or EM makers may be detected using antenna detectors.

In some examples, augmented reality (AR) systems and virtual reality systems may be incorporated with surgical navigation systems. Augmented reality systems may include an augmented reality device, headset, or glasses-like structure that allows a wearer to observe real world objects supplemented with additional rendered images on a lens of the augmented reality device, headset, or glasses-like structure. Accordingly, augmented reality devices may be integrated with surgical navigation systems to provide additional information to a medical professional. That is, augmented reality devices may augment the medical professional's real world view of a patient or objects with imaging data such as pre-operative imaging data, surgical instrument models, real-time patient vital information, and/or pre-operative plan information.

Figure 3:
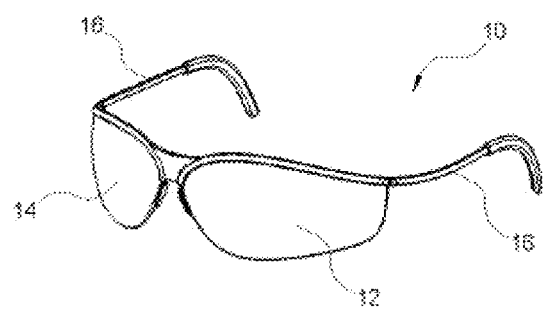
FIG. 3 illustrates a perspective view of an augmented reality device, in accordance with an example of the present application.

Reference is now made to FIG. 3, which illustrates a perspective view of an augmented reality device 10, in accordance with an example of the present application. The augmented reality device 10 may include a transparent or near transparent display screen configured adjacent a user's eye(s) such that the augmented reality device 10 may provide a field of view through the display screen. The augmented reality device 10 may be configured to display objects on the display screen to augment a user's view of the real world. For example, the augmented reality device 10 illustrated in FIG. 3 may be configured as a pair of glasses with a left display/lens 12, a right display/lens 14, and a pair of arms 16 for fitting over the top and back of the user's ears. In some examples, the augmented reality device 10 may include the left display/lens 12 and the right display/lens 14 for displaying pairs of stereoscopic images for creating or enhancing the illusion of depth in the pairs of stereoscopic images.

Figure 4:
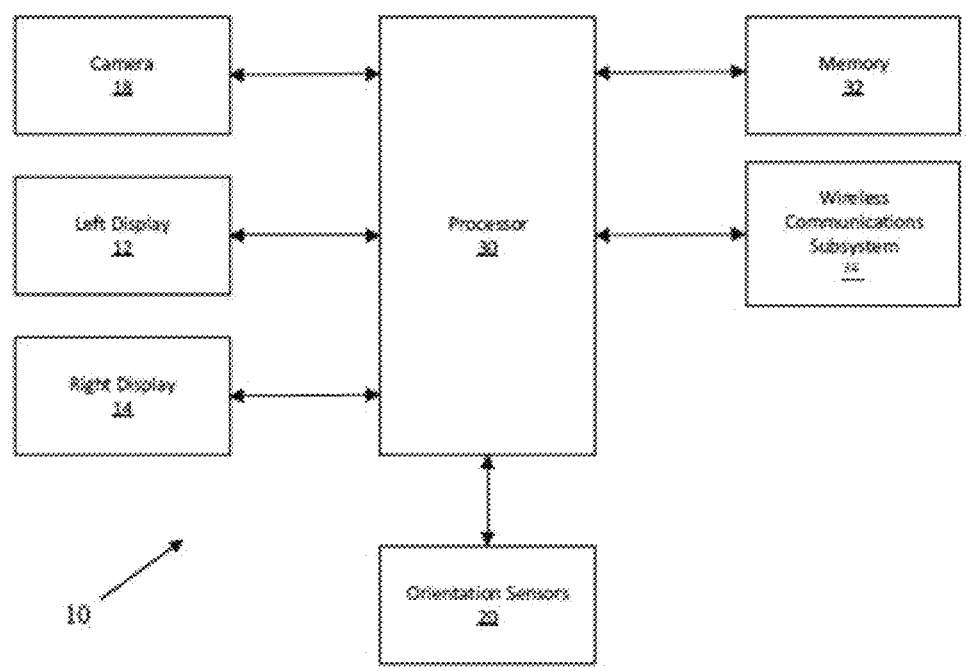
FIG. 4 illustrates a block diagram of the augmented reality device of FIG. 3, in accordance with an example of the present application.

Reference is now made to FIG. 4, which illustrates a block diagram of the augmented reality device 10 of FIG. 3, in accordance with an example of the present application. The augmented reality device 10 may include a processor 30, memory 32, a left display/lens 12, and a right display/lens 14. The left display/lens 12 and the right display/lens 14 may be integrated with transparent or semi-transparent lenses or visors through which a user, who may be wearing the augmented reality device 10, may view the real world. Images being displayed on the left display/lens 12 and the right display/lens 14 may be displayed within the user's field of view or line-of-sight of the real world.

The augmented reality device 10 may include orientation sensors 20 for tracking or determining changes in position and/or orientation of the augmented reality device 10 in a coordinate system associated with the real world. The augmented reality device 100 may be configured to display images in the left display/lens 12 or the right display/lens 14 according to changes to the user's field of view or line-of-sight of the real world through the left display/lens 12 or the right display/lens 14, such that images displayed concurrent with the user's view of the real world may appear as if they were positioned in the real world. The orientation sensors 20 may include at least one of accelerometers, gyroscopes, proximity sensors, or any other sensors or devices for providing position or orientation information relating to the augmented reality device 10.

The augmented reality device 10 may include a camera 18 (or multiple cameras). The camera 18 may be oriented in substantially the same direction as the field of view when the augmented reality device 10 is worn by the user. The camera 18 may be configured for identifying objects in the field of view of the augmented reality device 10 and for correlating or registering the identified objects in an augmented reality coordinate space or any other coordinate space. The camera 18 may also be configured for gesture recognition or other user input functions.

The augmented reality device 10 may also include a communication subsystem 34. The communication subsystem 34 may be a wireless communication subsystem and may be configured for enabling the augmented reality device 10 to communicate with remote systems or remote computing devices. In some examples, the communication subsystem 34 may communicate with a handheld device for receiving user input. Some examples of handheld devices may include a wand for gesture input, a mobile device, a smartwatch, a keyboard, a mouse, or the like. In some examples, the communication subsystem 34 may enable communications with remote computing devices, including computing servers. In some examples, the communication subsystem 34 may communicate with computing devices such as a surgical navigation system 200 (FIG. 2) in an operating room environment. Example communication protocols may include IEEE 802.11 (WiFi), Bluetooth™, near field communication protocols, ZigBee™, or any other suitable type of communication protocols.

The augmented reality device 10 may be configured to be worn like glasses or a headset by a user. The examples components described above may be incorporated into the augmented reality device 10 or may be partially enclosed in a nearby computing device and coupled to the augmented reality device 10 via a wired or wireless communication link. Description of other components of the example augmented reality device 10 have been omitted for ease of exposition and for clarity, including components such as power supplies, battery sources, other electronic circuitry, etc.

In some examples, the augmented reality device 10 may overlay pre-operative scan data on the medical professional's view of the real-world patient such that the medical professional may view three-dimensional CT scan data aligned with a patient's head. In another example, the augmented reality device 10 may render "dashboard" information, such as patient vitals or other monitored data, such that the medical professional may view the dashboard information in the medical professional's peripheral vision while performing the medical procedure. For example, the augmented reality device 10 may maintain rendering of the dashboard information in the medical professional's field of view irrespective of what direction the augmented reality device 10 may be oriented towards. In another example, the augmented reality device 10 may render pre-operative plan information, such as craniometrical cut-lines for opening access to a skull, so as to guide the medical professional during the surgical procedure. It may be appreciated from the description herein that a range of other possible information may be displayed by an augmented reality device 10 to assist the medical professional with planning, testing, practicing, or performing medical procedures.

Figure 5:
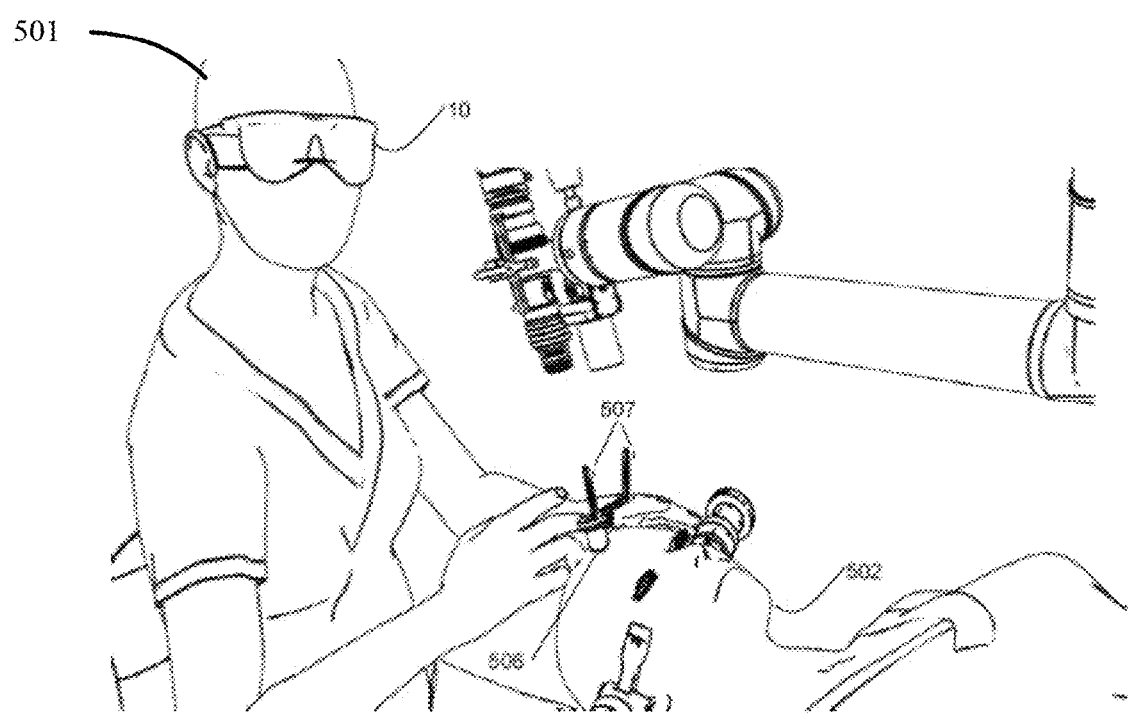
FIG. 5 illustrates an augmented reality device configured to operate with a surgical navigation system within an operating room environment for a port-based surgical procedure, in accordance with an example of the present application.

Reference is now made to FIG. 5, which illustrates an augmented reality device 10 configured to operate with a surgical navigation system within an operating room environment for a port-based surgical procedure, in accordance with an example of the present application. Although the surgical navigation system and the augmented reality device 10 is illustrated for use during an access-port surgical procedure, the surgical navigation system may be setup for other types of procedures, including spinal procedures, heart procedures, or any other type of procedure. In the illustrated example, a medical professional may be resecting a tumor or other tissue from a brain of a patient 502 through an access port 506. In some examples, an external scope may be coupled to a robotic or positioning arm, and the external scope may be configured to allow the medical professional to view a magnified view of tissue through an opening of the access port 506. Images may be captured by the external scope and may be displayed on a visual display, such as a display device mounted adjacent or in close proximity to the medical professional. The medical professional may utilize displayed images on the display device to view the surgical site. However, with such an environment, the medical professional may need to view displayed images on the display device thereby shifting visual focus from the patient or medical procedure site to the display device.

Thus, the medical professional 501 may wear the augmented reality device 10 and the augmented reality device 10 may provide the medical professional with a convenient method for augmenting the medical professional's real world view with display data. For example, the display data may be provided or rendered on the left display/lens 12 and/or the right display/lens 14 (FIG. 4) and may include pre-operative scan data, a model of surgical instruments, patient vital information, and/or pre-operative plan information.

Active or passive fiducial markers 507, such as spherical markers, may be arranged in a fixed geometrical arrangement in fixed relation to portions of a patient, a surgical site, surgical instruments, or objects within a surgical navigation environment. Accordingly, a tracking device, such as an optical imaging device, may detect the active or passive fiducial markers 507 such that position and/or orientation information of objects associated with the active or passive fiducial markers 507 may be determined.

Figure 6A:
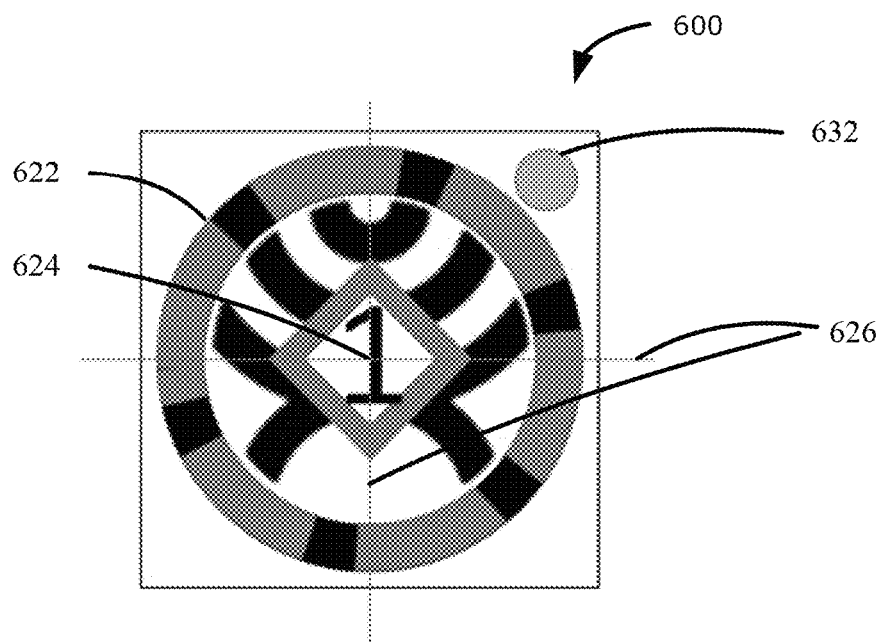
FIG. 6A illustrates a reference body 600 affixable to objects tracked by a surgical navigation system, in accordance with an example of the present application.

Reference is now made to FIG. 6A, which illustrates a reference body 600 affixable to an object tracked by a surgical navigation system, in accordance with an example of the present application. Simultaneous reference will be made to FIG. 6B, which illustrates an exploded perspective view of the reference body 600 of FIG. 6A, for highlighting features described herein.

Figure 6B:
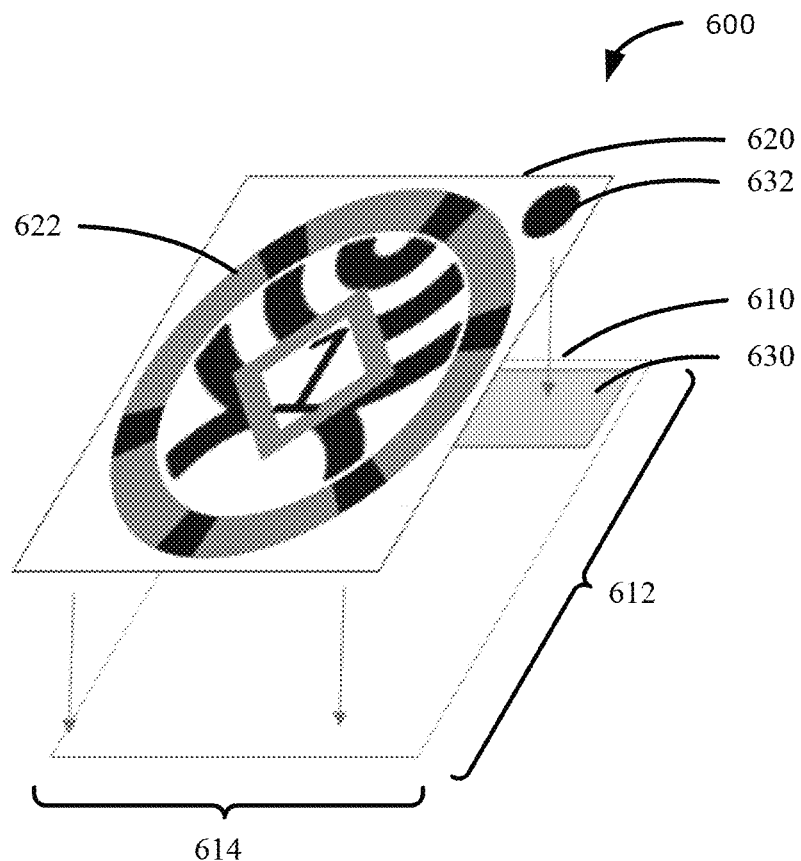
FIG. 6B illustrates an exploded perspective view of the reference body 600 of FIG. 6A.

As illustrated in FIG. 6B, the reference body 600 may include a substrate 610 having a substrate surface area. The substrate surface area may be defined by a length 612 and a width 614 of the substrate 610. The substrate may be constructed of any rigid, flexible, or semi-flexible material suitable for being affixed to objects tracked by the surgical navigation system. For example, the substrate may be a sticker backing material such that one surface of the substrate may include adhesive material for adhering the sticker backing material to objects being tracked. The substrate may be constructed of any other materials for supporting the reference body 600 having features described herein.

The reference body 600 may include a first layer 620 affixed to the substrate 610. The first layer 620 may include a first totem pattern 622 at a first position centered at an origin 624 of orientation axes 626. For example, the orientation axes 626 may be an x-axis and a y-axis of a Cartesian coordinate system. Although the first totem pattern 622 illustrated in FIG. 6A is centered at the origin 624 of orientation axes 626, the first totem pattern 622 may be positioned at any other position on the first layer 620 and have a pre-configured or pre-determined position identifiable relative to the origin 624.

The first totem pattern 622 may include one or more unique identifiable features distinguishing the first totem pattern 622 from another totem pattern. As will be illustrated in the present application, the first totem pattern 622 and other totem patterns may include unique identifying features such as bar codes, unique symbols or designs, or the like for differentiating that totem pattern from other totem patterns. In some examples, when the tracking system 213 (FIG. 2) of the surgical navigation system 200 (FIG. 2) includes an optical imaging device, the first totem pattern 622 and other totem patterns may include optically detectable features that may uniquely identify that totem pattern from other totem patterns.

The reference body 600 may also include a retroreflective portion 630 affixed to the substrate at a second position from the origin 624. The retroreflective portion 630 may include a surface that may reflect light back to a light source such that the reflected light may be minimally scattered. For example, the retroreflective portion 630 may reflect light rays back along a light ray direction that is parallel to but opposite in direction than light transmitted from the light ray source. For example, the tracking system 213 may emit infrared light in a direction towards the retroreflective portion 630 and the retroreflective portion 630 may reflect the incident infrared light back to the optical imaging device in a direction that is parallel to but opposite to the direction of the incident infrared light. Accordingly, the retroreflective portion 630 of the reference body 600 may be detectable by the tracking system 213 and the surgical navigation system 200 may determine position information of the reference body 600 based on the detection of the retroreflective portion 630 of the reference body 600. That is, the surgical navigation system 200 may determine the position of the tracked object by determining the position based on electromagnetic reflection from respective retroreflective portions being detected by the optical imaging device.

In some examples, the surgical navigation system 200 may determine the position of the tracked object by determining the position based on electromagnetic emissions from respective retroreflective portions being detected by the optical imaging device. The retroreflective portion 630 may include active electromagnetic emitters and the retroreflective portion 630 may emit, for example, infrared light that may be detected by the optical imaging device.

In some scenarios, it may be challenging to accurately position a retroreflective portion 630 at known or pre-configured positions from the origin 624. That is, it may be incrementally costly to employ precise pick-and-place operations for accurately placing retroreflective portions 630 at known positions from the origin 624. Manufacturing operations for cutting through-holes or other through-shapes in materials, however, may be less challenging and less expensive as compared to pick-and-place operations. Thus, in some examples, the first layer 620 may also include a first through-hole 632 associated with the first totem pattern 622 such that the retroreflective portion 630 may be detectable by the surgical navigation system 200 subject to positioning of the first through-hole 632.

For example, the first through-hole 632 may be centered at the second position from the origin 624. That is, the first through-hole 632 may be at a pre-configured or known position from the origin 624 of the orientation axes 626. Further, the retroreflective portion 630 may be affixed between the substrate 610 and the first layer 620 such that the retroreflective portion 630 is detectable by the tracking system 213 (e.g., optical imaging device) via the first through-hole 632. The combination of the first layer 620 having the first through-hole 632, the retroreflective portion 630, and the substrate 610 provides a "retroreflective disk" detectable by the surgical navigation system.

In some examples, the surface area of the retroreflective portion 630 may be less than the substrate surface area. As illustrated in FIG. 6B, the retroreflective portion 630 may be a rectangular strip of retroreflective material, and the surface area of the retroreflective portion 630 may be less than the substrate surface area. Further, the surface area of the retroreflective portion 630 may be greater than an area of the first through-hole 632. For example, because the first through-hole 632 may have a circular shape, the first through-hole 632 may have a circular area, where the circular area may be less than the surface area of the retroreflective portion 630. Because the surface area of the retroreflective portion 630 may be greater than the area of the first through-hole 632 and because the first through-hole 632 is positioned adjacent the retroreflective portion 630, a subset of the retroreflective portion 630 may be detectable by the tracking system 213, such as an optical imaging device, via the first through-hole 632. Thus, it may be appreciated that the retroreflective portion 630 may be placed relatively coarsely between the first layer 620 and the substrate 610, yet exposing the retroreflective portion 630 as a retroreflective disk to the surgical navigation system via the first through-hole 632 results in an accurate pre-configured positioning of the retroreflective disk relative to the origin 624.

It will be appreciated that, in some examples, the surgical navigation system 200 may determine position information of the reference body 600 in the surgical coordinate space based on the first totem pattern 622 or the retroreflective disk. That is, position information may be deduced based on detected markers. However, the surgical navigation system 200 may be unable to determine orientation of the reference body 600 in the surgical coordinate space based solely on the first totem pattern 622 and the retroreflective portion 630 exposed via the first through-hole 632. To determine orientation of the reference body 600, a greater number of reference points may be required.

Although the above example describes providing a "retroreflective disk" based on the combination of the first layer 620 having the first through-hole 632, the retroreflective portion 630, and the substrate 610, in some other examples, the retroreflective portion may be provided as a circular-shape and may be adhered to the surface of the first layer at the second position such that the retroreflective disk may be detectable by the surgical navigation system. Further, in some examples, the reference body 600 may be configured not to include any retroreflective portion or any retroreflective disks and may include one or more totem patterns positioned on the first layer 620 without retroreflective disks.

Figure 7:
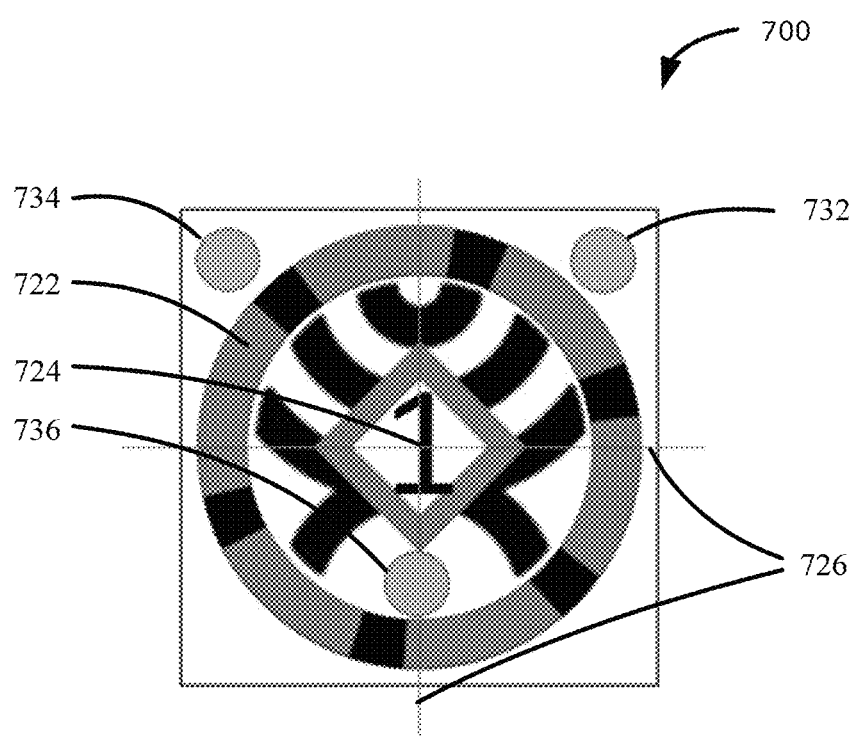
FIG. 7 illustrates a reference body 700 affixable to objects tracked by a surgical navigation system, in accordance with another example of the present application.

Reference is now made to FIG. 7, which illustrates a reference body 700 affixable to objects tracked by a surgical navigation system, in accordance with another example of the present application. The reference body 700 may include a first totem pattern 722 at a first position centered at an origin 724 of orientation axes 726. For example, the orientation axes 726 may be an x-axis and a y-axis of a Cartesian coordinate system. Although the first totem pattern 722 illustrated in FIG. 7 is centered at the origin 724 of orientation axes 726, the first totem pattern 722 may be positioned at any other position on first layer of the reference body 700, having a pre-configured or pre-determined position identifiable relative to the origin 724. Further, although the orientation axes 726 may be associated with a Cartesian coordinate system, in some examples, the orientation axes 726 may be any other coordinate system. It may be appreciated that the first totem pattern 722 and the origin 724 of orientation axes 726 of FIG. 7 may be similar to the first totem pattern 622 and the origin 624 of orientation axes 626 illustrated in FIGS. 6A and 6B.

In some examples, three or more marks may be required to uniquely identify objects, and four or more marks may be required to identify a pose, such as position and/or orientation, of objects to which marks may be associated. Thus, in some examples, the reference body 700 may include a first layer having three or more through-holes associated with the first totem pattern 722, where each of the three or more through-holes may be positioned at a respective known position or distance from the origin 724 of orientation axes 726. For example, the reference body 700 may include the first layer having a first through-hole 732, a second through-hole 734, and a third through-hole 736. Each of the first through-hole 732, the second through-hole 734, and the third through-hole 736 may be positioned at a pre-configured or known position relative to the origin 724.

The reference body 700 may also include a retroreflective portion (not explicitly illustrated) affixed between the substrate and the first layer such that the retroreflective portion may be detectable by a tracking system 213 (FIG. 2), such as an optical imaging device, via each of the three or more through-holes. The tracking system 213 may detect each of the three or more through-holes as retroreflective disks for determining a pose of the reference body 700 in the surgical coordinate space.

Although examples described herein include may retroreflective portions detectable by tracking systems 213 based on incident and reflected electromagnetic emissions (e.g., infrared light, visible light, or other forms of electromagnetic radiation), other forms of markers may be included at known positions associated with the first through-hole 732, the second through-hole 734, and the third through-hole 736. For example, electromagnetic coils or touchpoint divots may be provided at the first through-hole 732, the second through-hole 734, and the third through-hole 736 locations.

For example, a reference body may include a substrate and a first layer affixed to the substrate. The first layer may include a first totem pattern at a first position centered at an origin of orientation axes. The first totem pattern may include a unique identifiable feature distinguishing the first totem pattern from another totem pattern. The reference body may also include at least one touch point divot for touch point registration of the first totem pattern. The at least one touchpoint divot may be a through-hole in the first layer and may be associated with the first totem pattern. The at least one touchpoint divot may be positioned at a respective known distance from the origin.

Figure 8:
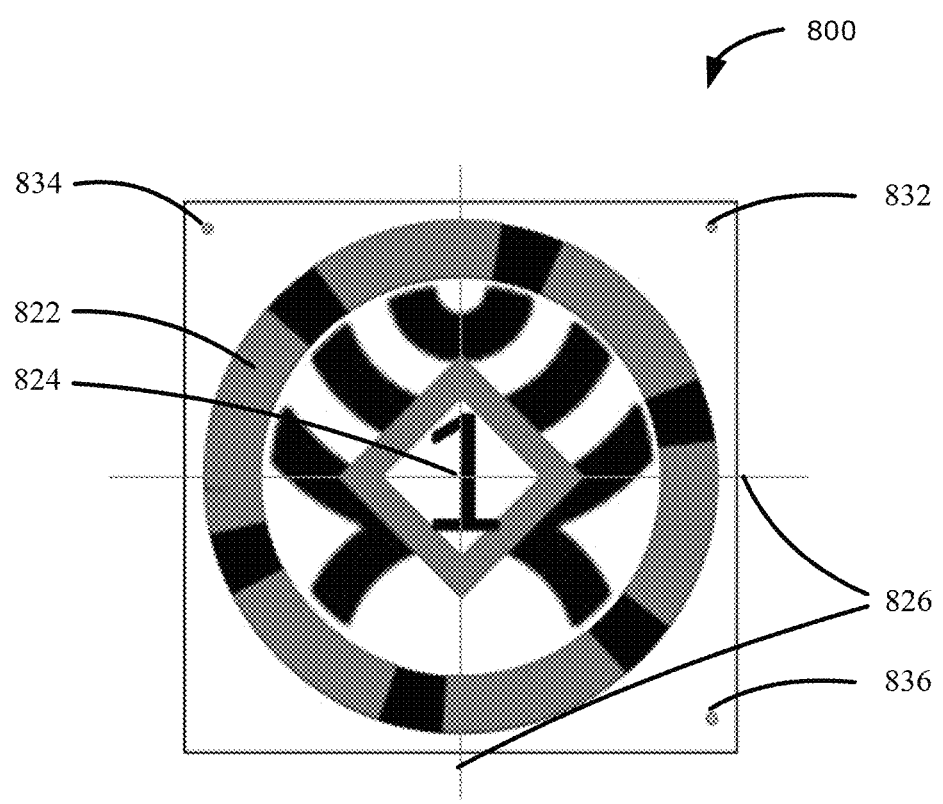
FIG. 8 illustrates a reference body 800 affixable to objects tracked by a surgical navigation system, in accordance with another example of the present application.

To illustrate, reference is now made to FIG. 8, which illustrates a reference body 800 affixable to objects tracked by a surgical navigation system, in accordance with another example of the present application. The reference body 800 may include a first layer having a first totem pattern 822 and an origin 824 of orientation axes 826 similar to the first totem pattern 622 and the origin 624 of orientation axes 626 illustrated in FIGS. 6A and 6B.

The reference body 800 may also include a plurality of touchpoint marks or divots positioned at known positions relative to the origin 824. For example, the reference body 800 may include a first touchpoint 832, a second touchpoint 834, and a third touchpoint 836. In some examples, the plurality of touchpoints may not be combined with retroreflective materials. The plurality of touchpoints may be recessed divots extending from the first layer to the substrate for touch point registration of the first totem pattern 822. For example, registration based on touchpoints at known or pre-configured positions may include operations such as: (1) identifying fiducial touchpoints on the reference body 800; (2) detecting touch operations of the fiducial touchpoints with an instrument that may be tracked by the tracking system 213 (FIG. 2); and (3) generating registration data relating to the position of the tracked instrument when the tracked instrument "touches" the fiducial touchpoints on the reference body. Accordingly, the reference body 800 may facilitate touchpoint registration operations for determining a pose of the reference body 800 (and the associated object being tracked) and/or registering the reference body 800 in the surgical coordinate space.

Although the reference bodies described above include a single totem pattern, such as the first totem pattern 622 in FIG. 6, in some examples, a reference body may include two or more totem patterns. To illustrate, reference is now made to FIG. 9, which illustrates a reference body 900 including a plurality of uniquely identifiable totem patterns, in accordance with an example of the present application. For example, in addition to a first totem pattern, a first layer of a reference body may include additional totem patterns.

Figure 9:
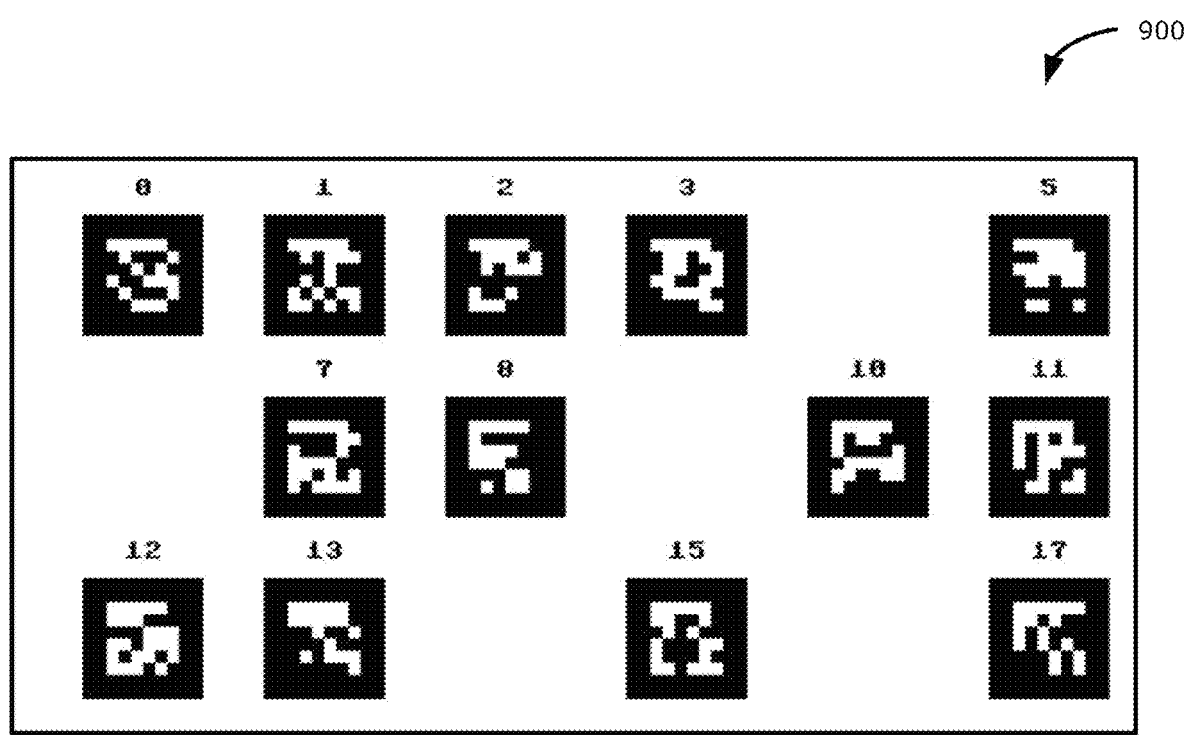
FIG. 9 illustrates a reference body 900 including a plurality of uniquely identifiable totem patterns, in accordance with an example of the present application.

The reference body 900 may be a rectangular shaped reference body including a first layer having the plurality of uniquely identifiable totem patterns. For ease of exposition, the totem patterns are identified using numbers 0 to 3, 5, 7, 8, 10 to 13, 15, and 17. Each of the totem patterns may include one or more unique identifiable feature distinguishing that totem pattern from another totem pattern. In some examples, each of the totem patterns may be non-overlapping with another totem pattern. As illustrated in FIG. 9, the first totem pattern (identified with number 0) includes a unique arrangement of blocks that may be distinguishable from each of the other totem patterns of the reference body 900.

In some examples, each of the totem patterns may be positioned on the first layer at a known position relative to other totem patterns such that a combination of the totem patterns is a marker group detectable by the surgical navigation system 200 (FIG. 2) as a composite totem pattern. The totem pattern identified by the number 8, for example, is positioned on the first layer of reference body 900 at a pre-configured or known distance from each of the other totem patterns. Accordingly, the surgical navigation system 200 may detect the arrangement of totem patterns of the reference body 900 and may: (1) identify or determine pose information based on each totem pattern individually; or (2) identify or determine pose information based on the combined arrangement of the plurality of totem patterns. That is, each totem pattern may be detected by the surgical navigation system 200 as an independent totem pattern or may be detected and considered by the surgical navigation system 200 as a cluster of reference marks providing a composite totem pattern. As will be apparent based on the description herein, when the surgical navigation system 200 considers the cluster of reference marks as a composite totem pattern, the surgical navigation system 200 may in some scenarios also rely on the unique identifiable characteristics of the individual totem patterns for determining a pose of the reference body 900. In some examples, the surgical navigation system 200 may rely on the unique identifiable characteristics when the individual totem patterns may be recognized or deciphered from a captured image of the reference body 900.

The reference body 900 including a combination of two or more arranged totem patterns may be desirable in scenarios when the reference body 900 may be used in an environment where totem pattern tracking accuracy may be compromised. Totem pattern tracking accuracy may diminish when an individual totem pattern may be indiscernible by the tracking system 213 of the surgical navigation system 200. For example, the at least one totem pattern may be indiscernible in an image captured by the tracking system 213 when the resolution of the captured image may be insufficient for resolving unique identifiable feature(s) of the at least one totem pattern. The resolution of the captured image may be insufficient for resolving unique identifiable feature(s) of the at least one totem pattern when the focal length setting of the tracking system 213 (e.g., optical imaging device) may cause the totem pattern to appear relatively small in the captured image. That is, focal length settings resulting in a wide-angle or "zoomed out" image may cause the totem pattern to appear small in the captured image. In another scenario, the at least one totem pattern may be indiscernible in an image captured by the tracking system 213 when the at least one totem pattern may be out of focus. For example, the focus settings of the tracking system 213 (e.g., optical imaging device) may cause the totem pattern to appear out-of-focus (e.g., blurry). To ameliorate some of the disadvantages of relying upon individual totem patterns for identifying tracked objects, it may be desirable to provide reference bodies having two or more totem patterns that may be detected (1) individually for identifying objects; and/or (2) in combination with other totem patterns based on pre-configured or known relationships between a plurality of totem patterns. That is, it may be desirable that the reference body 900 be detectable as an aggregation of single independent totem patterns or as a combination of totem patterns, where each totem pattern in the combination is spatially positioned according to a pre-configured totem pattern layout.

Figure 10:
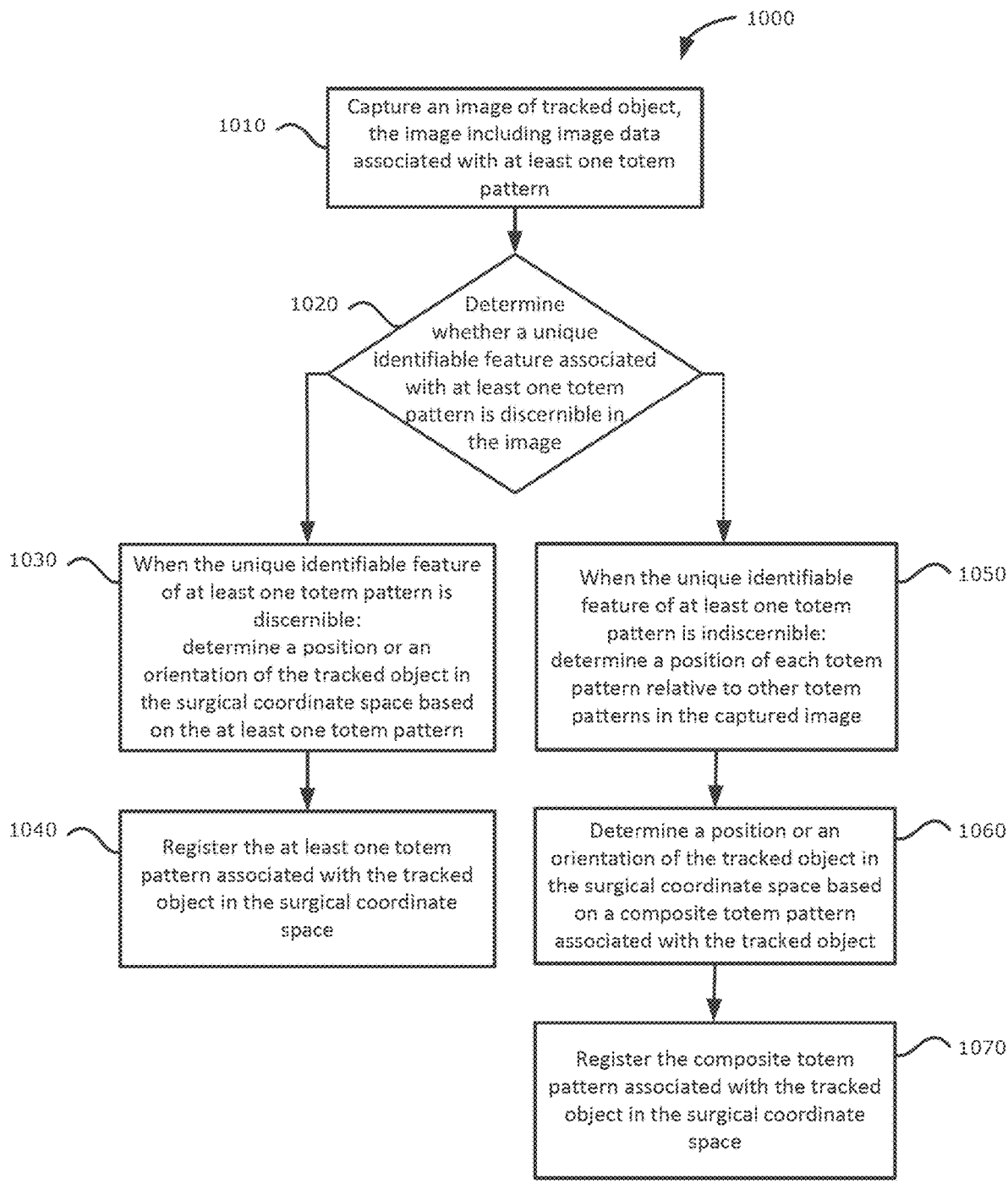
FIG. 10 illustrates a flowchart of a method of tracking an object in a surgical coordinate space by a surgical navigation system, in accordance with an example of the present application.

Reference is now made to FIG. 10, which illustrates a flowchart of a method 1000 of tracking an object in a surgical coordinate space by a surgical navigation system 200 (FIG. 2) including an optical imaging device. The tracked object may have a reference body affixed thereto. The reference body may comprise a substrate and a first layer affixed to the substrate. The first layer may include a plurality of totem patterns. Each totem pattern may have a unique identifiable feature distinguishing that totem pattern from another totem pattern in the plurality of totem patterns. A position of each totem pattern relative to other totem patterns may be pre-configured. For example, the reference body 900 of FIG. 9 is an example of a reference body having a plurality of totem patterns, where a position of each totem pattern relative to other totem patterns may be pre-configured or known. In some other examples, relative positions of each totem pattern relative to other totem patterns may be determined during a calibration phase for the surgical navigation system 200. That is, relative positions of each totem pattern relative to other totem patterns may be determined when the surgical navigation system 200 is being configured or setup for a target medical procedure. Once positions of each totem pattern relative to other totem patterns may be determined, a group of totem patterns may form a composite totem pattern, as described herein. The tracking system 213 (FIG. 2) of the surgical navigation system 200 may include the optical imaging device.

At operation 1010, the surgical navigation system 200 may capture an image of the tracked object. The image may include image data associated with at least one totem pattern. If the surgical navigation system 200 captures an image of the tracked object at a short focal length, the captured image may include the reference body including a plurality of totem patterns. For example, the reference body 900 of FIG. 9 may include a plurality of totem patterns. If the totality of totem patterns is captured in the image, the totality of the totem patterns may be a composite totem pattern. Conversely, if the surgical navigation system 200 captures an image of the tracked object at a long focal length, the captured image may include fewer number of totem patterns. That is, the captured image may not include image data associated with some of the totem patterns of the reference body 900. Thus, in some examples, the surgical navigation system 200 may rely on individual totem patterns for identifying objects or determining pose information.

At operation 1020, the surgical navigation system 200 may determine whether a unique identifiable feature associated with at least one totem pattern is discernible in the captured image. For example, at least one totem pattern may be indiscernible when the resolution of the captured image may be insufficient for resolving the unique identifiable feature of the at least one totem pattern. In another example, the at least one totem pattern may be indiscernible when the at last one totem pattern within the captured image may be out of focus.

When the unique identifiable feature of at least one totem pattern is discernible, at operation 1030, the surgical navigation system 200 may determine a position or an orientation of the tracked object in the surgical coordinate space based on the at least one totem pattern.

In some examples, the surgical navigation system 200 may include an optical imaging device with an infrared transmitter and receiver for identifying reference bodies. The at least one totem pattern that is discernible may be included in a reference body similar to the reference body 700 of FIG. 7. When the infrared transmitter transmits an infrared emission, retroreflective portions exposed via through-holes (e.g., retroreflective disks) may reflect infrared emissions back to the optical imaging device and the surgical navigation system 200 may determine a position or an orientation of the tracked object based on the totem pattern and the retroreflective portions detectable via the three through-holes. That is, the combination of the totem pattern and the "retroreflective disks" at known positions relative to the origin may provide the surgical navigation system 200 with information for determining position and orientation of the reference body in the surgical coordinate space.

At operation 1040, the surgical navigation system 200 may register the at least one totem pattern associated with the tracked object in the surgical coordinate space. The surgical navigation system 200 may perform registration according to any of known registration techniques.

When the unique identifiable feature of at least one totem pattern is indiscernible, at operation 1050, the surgical navigation system 200 may determine a position of each totem pattern relative to other totem patterns in the captured image such that a combination of totem patterns within the captured image is a marker group detectable by the surgical navigation system 200 as a composite totem pattern.

If the surgical navigation system 200 captures an image of the entire reference body 900 illustrated in FIG. 9, the surgical navigation system 200 may determine that unique identifiable features of the totem patterns may be indiscernible if the captured image is a low resolution image and the unique identifiable features of the depicted totem patterns cannot be recognized. In another example, the surgical navigation system 200 may determine that unique identifiable features of the totem patterns may be indiscernible if the unique identifiable features of the depicted totem patterns are out of focus.

Accordingly, at operation 1050, the surgical navigation system 200 may determine that the combination of totem patterns within the reference body 900 is a composite totem pattern and, thus, determine a position of each totem pattern relative to other totem patterns in the captured image.

At operation 1060, the surgical navigation system may determine a position or an orientation of the tracked object in the surgical coordinate space based on the composite totem pattern associated with the tracked object.

At operation 1070, the surgical navigation system 200 may register the composite totem pattern associated with the tracked object in the surgical coordinate space. The surgical navigation system 200 may perform registration according to any number of known registration techniques.

In some examples, when the surgical navigation system 200, at operation 1020, may be unable to discern or recognize at least one unique identifiable feature associated with at least one totem pattern so as to distinguish that totem pattern from other totem patterns, the surgical navigation system 200 may perform operations for ameliorating the inability to discern unique identifiable features from totem patterns. For instance, the tracking system 213 may adjust a focus setting of the optical imaging device and, subsequently, the surgical navigation system 200 may determine whether a unique identifiable feature may be discernible in the re-focused image capture.

If focus setting adjustments to the optical imaging device do not remedy the indiscernible totem patterns, the surgical navigation system may carry out operation 1050, operation 1060, and operation 1070, as described above. In contrast, if focus setting adjustments to the optical imaging device appear to correct deficiencies in detecting token pattern details, the surgical navigation system 200 may utilize individual token patterns on their own for registration.

Although the above example operations describe adjusting focus settings when attempting to ameliorate inabilities to discern totem patterns from captured images, it may be appreciated that other optical imaging device settings may be adjusted for attempting to ameliorate inabilities to discern totem patterns. For example, shutter speed or aperture settings may be adjusted to alter image brightness characteristics that may affect discernibility or detectability of token patterns.

As described, it may be desirable to provide one or more reference bodies affixable to objects that may be tracked by surgical navigation systems, such that the reference bodies may be uniquely identifiable. Once reference bodies (and associated objects on which reference bodies may be affixed) are registered in the surgical coordinate space, in some examples, it may be desirable to associate augmented reality overlays with a tracked object based on at least one totem pattern or composite totem pattern and to display the augmented reality overlays on a display or an augmented reality device to augment a real world view of the tracked object. That is, the at least one totem pattern or composite totem pattern may be used to anchor a position or orientation of an augmented realty overlay to captured images. In some examples, augmented reality overlays may include pre-operative image data associated with the real world view of the tracked object. Accordingly, augmented reality overlays may be generated from pre-operative images of a patient and displayed by an augmented reality device such that a user of that augmented reality device may view the patient (in the real world) along with augmented images or information provided by the augmented reality overlay.

In some examples, a reference body may also include a retroreflective portion associated with each of a plurality of totem patterns of the reference body. The respective retroreflective portions may be positioned at known positions from an origin of orientation axes of respective totem patterns and the retroreflective portions may be detectable by an optical imaging device of the surgical navigation system. For example, the surgical navigation system may be configured to transmit electromagnetic emissions (e.g., infrared or visible light emissions) in a direction of the reference body, and the respective retroreflective portions may reflect the electromagnetic emissions back to an optical imaging device of the surgical navigation system. In some examples, determining a position of a tracked object may include determining a position based on reflected light from respective retroreflective portions being detected by an optical imaging device. That is, the surgical navigation system may determine a position or orientation of the reference body based on detection of the totem pattern and/or retroreflective portion(s) of the reference body.

In some examples, the reference body may include a retroreflective portion having three or more retroreflective markers, each of the three or more retroreflective markers positioned at known positions from the origin position of orientation axes associated with the respective totem patterns. In some examples, determining the position or the orientation of a tracked object in a surgical coordinate space may include determining a position or orientation of the reference body using touch point registration based on touch points at the three or more retroreflective markers of the respective totem patterns.

Figure 11:
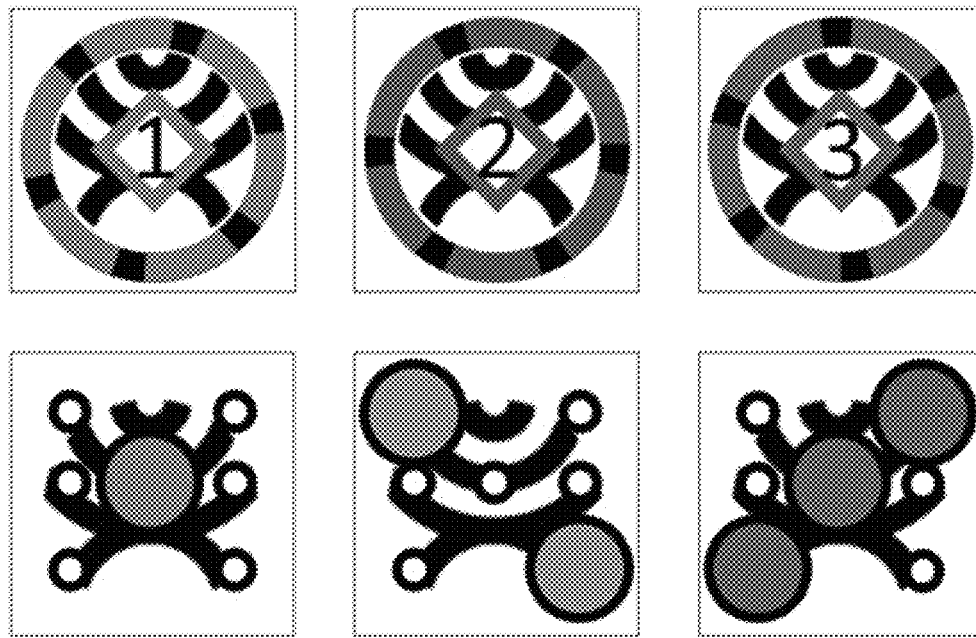
FIG. 11 illustrates example totem patterns, in accordance with examples of the present application.
Figure 12:
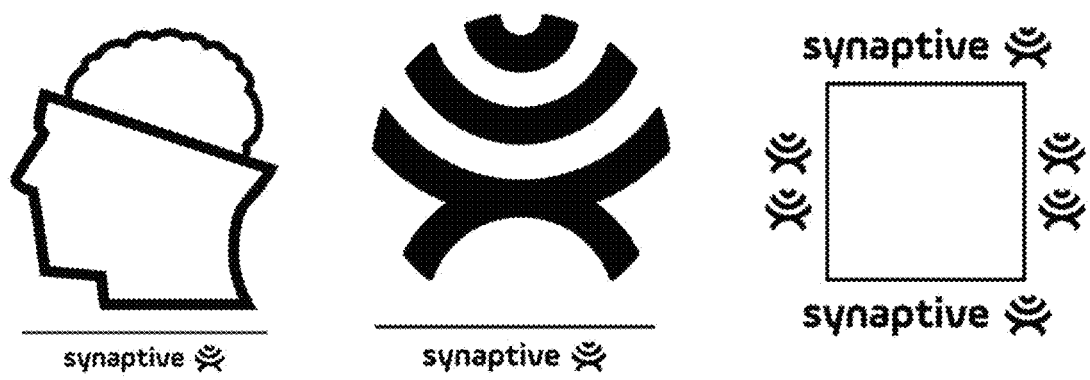
FIG. 12 illustrates example totem patterns, in accordance with examples of the present application.

Reference is now made to FIGS. 11 and 12, which illustrates example totem patterns, in accordance with examples of the present application. As illustrated in FIG. 11, each of the totem patterns may be distinguishable from another totem pattern based on unique features. For example, unique features may include different text (e.g., "1", "2", or "3"). In other examples, unique features may include different configuration of circular or curved line shapes. In some examples, if a surgical navigation system is configured to detect colors, unique features may be differentiated based on colors. As illustrated in FIG. 12, each of the totem patterns may be distinguishable from another totem pattern based on graphical designs. It will be appreciated that reference bodies described herein may include totem patterns having features of quick response (QR) codes, bar codes, or any symbols having sufficiently identifiable features that may be used to distinguish that totem pattern from other totem patterns.

As described herein, surgical navigation systems may determine position and/or orientation of tracked objects by detecting reference bodies affixed to tracked objects. In some examples, surgical navigation systems may not require continuous, real-time detection of the reference bodies described herein, but may be configured to update reference body positions and/or orientations when a detected line of sight may be established.

In some examples, optical imaging devices of surgical navigation systems may be associated with a first imaging modality. The first imaging modality may be a video imaging device. For example, the video imaging device may optically capture images of reference bodies (e.g., totem patterns and/or retroreflective disks). Further, the retroreflective portion or a substrate may include a contrast material detectable by a second imaging device associated with a second imaging modality. For instance, the second imaging modality may include one of magnetic resonance imaging or computed tomography imaging. Accordingly, example reference bodies described herein may be configured for multi-modality registration methods that may be used to register images acquired by different scanning or sensor technologies.

Certain adaptations and modifications of the described embodiments can be made. Therefore, the above discussed embodiments are considered to be illustrative and not restrictive.

What is claimed is:

1. A method of tracking an object in a surgical coordinate space by a surgical navigation system including an optical imaging device, the tracked object having a reference body affixed thereto, the reference body comprising a substrate and a first layer affixed to the substrate, the first layer including a plurality of totem patterns, each totem pattern having a unique identifiable feature distinguishing that totem pattern from another totem pattern in the plurality of totem patterns, the method comprising:

capturing an image of the tracked object, the image including image data associated with at least one totem pattern;

determining whether a unique identifiable feature associated with at least one totem pattern is discernible in the image;

when the unique identifiable feature associated with at least one totem pattern is discernible:

determining a position or an orientation of the tracked object in the surgical coordinate space based on the at least one totem pattern; and registering the at least one totem pattern associated with the tracked object in the surgical coordinate space; and when the unique identifiable feature associated with at least one totem pattern is indiscernible:

determining a position of each totem pattern relative to other totem patterns in the captured image such that a combination of totem patterns within the captured image is a marker group detectable by the surgical navigation system as a composite totem pattern;

determining a position or an orientation of the tracked object in the surgical coordinate space based on the composite totem pattern associated with the tracked object; and registering the composite totem pattern associated with the tracked object in the surgical coordinate space.

2. The method of claim 1, wherein the at least one totem pattern is indiscernible when resolution of the captured image is insufficient for resolving the unique identifiable feature of the at least one totem pattern.

3. The method of claim 1, wherein the at least one totem pattern is indiscernible when the at least one totem pattern within the captured image is out of focus.

4. The method of claim 1, wherein when the at least one totem pattern is indiscernible, prior to determining the position of each totem pattern relative to other totem patterns in the captured image, the method further comprising:

adjusting focal setting of the optical imaging device; and when the unique identifiable feature of the at least one totem pattern continues to be indiscernible:

determining the position of each totem pattern relative to other totem patterns in the captured image such that the combination of totem patterns within the captured image is the marker group detectable by the surgical navigation system as the composite totem pattern; and determining the position or the orientation of the tracked object in the surgical coordinate space based on the composite totem pattern associated with the tracked object.

5. The method of claim 1, further comprising:

associating an augmented reality overlay with the tracked object based on the at least one totem pattern or the composite totem pattern; and displaying the augmented reality overlay on a display or an augmented reality device to augment a real world view of the tracked object.

6. The method of claim 5, wherein the augmented reality overlay is pre-operative image data associated with the real world view of the tracked object.

7. The method of claim 1, wherein the reference body further includes a retroreflective portion associated with each of the totem patterns, the retroreflective portion positioned at a known position from an origin of orientation axes associated with respective totem patterns such that the retroreflective portion is detectable by the optical imaging device, and wherein determining the position of the tracked object includes determining the position based on electromagnetic emission or reflection from respective retroreflective portions being detected by the optical imaging device.

8. The method of claim 7, wherein the retroreflective portion associated with each of the totem patterns includes three or more retroreflective markers, each of the three or more retroreflective markers positioned at known positions from the origin position of orientation axes associated with the respective totem patterns, and wherein determining the orientation of the tracked object includes determining the orientation based on electromagnetic emission incident on the three or more retroreflective markers associated with each of the totem patterns being detected by the optical imaging device.

9. The method of claim 1, wherein the reference body further includes touchpoint divots associated with each of the totem patterns, each of the touchpoint divots positioned at known positions from the origin position of orientation axes associated with the respective totem patterns, and wherein determining the position or the orientation of the tracked object in the surgical coordinate space includes determining the position or the orientation using touch point registration based on touch points at the touchpoint divots of the respective totem patterns.

10. A surgical navigation system to track an object in a surgical coordinate space, the tracked object having a reference body affixed thereto, the reference body comprising a substrate and a first layer affixed to the substrate, the first layer including a plurality of totem patterns, each totem pattern having a unique identifiable feature distinguishing that totem pattern from another totem pattern in the plurality of totem patterns, the surgical navigation system comprising:

a processor;

an optical imaging device coupled to the processor; and a memory coupled to the processor and storing processor-readable instructions that, when executed, cause the processor to perform the method according to claim 1.

* * * * *